United States Patent [19]

Tung et al.

[11] Patent Number: 4,950,816

[45] Date of Patent: Aug. 21, 1990

[54] PURIFICATION OF 1,1-DICHLORO-1-FLUOROETHANE

[75] Inventors: Hsueh S. Tung, Williamsville; Addison M. Smith, Amherst, both of N.Y.

[73] Assignee: Allied-Signal Inc., Morris Township, Morris County, N.J.

[21] Appl. No.: 451,074

[22] Filed: Dec. 15, 1989

[51] Int. Cl.$^5$ .............................................. C07C 17/38
[52] U.S. Cl. .................................... 570/179; 570/164
[58] Field of Search ................................ 570/164, 179

[56] References Cited

U.S. PATENT DOCUMENTS 3,026,359  3/1962  Mastrangelo ..................... 570/179
3,833,676  9/1974  Ukaji et al. .
4,849,558  7/1989  Goodman .

OTHER PUBLICATIONS

A. L. Henne et al., *J. Am. Chem. Soc.* 65, 1271 (1943).

*Primary Examiner*—Alan Siegel
*Attorney, Agent, or Firm*—Melanie L. Brown; Jay P. Friedenson

[57] ABSTRACT

The present invention provides a process for the purification of 1,1-dichloro-1-fluoroethane comprising the steps of: (a) reacting anhydrous hydrogen fluoride with 1,1,1-trichloroethane or vinylidene chloride containing dichloroacetylene to form 1,1-dichloro-1-fluoroethane; and (b) passing the 1,1-dichloro-1-fluoroethane through activated carbon to substantially remove unsaturated impurities. In particular, the present process reduces the amounts of dichloroacetylene and vinylidene chloride in the 1,1-dichloro-1-fluoroethane product so as to meet the current specifications set forth by the Panel for Advancement of Fluorocarbon Test.

The purified 1,1-dichloro-1-fluoroethane product is useful as a blowing agent and a solvent.

14 Claims, No Drawings

PURIFICATION OF 1,1-DICHLORO-1-FLUOROETHANE

FIELD OF THE INVENTION

The present invention relates to purification of 1,1-dichloro-1-fluoroethane.

CROSS-REFERENCE TO RELATED APPLICATION

Co-pending, commonly assigned patent application Ser. No. 290,127 filed Dec. 27, 1988 discloses a process for the preparation of 1,1-dichloro-1-fluoroethane.

BACKGROUND OF THE INVENTION

Trichlorofluoromethane (known in the art as CFC-11) is currently available in commercial quantities and is used as a blowing agent for rigid urethane thermo-insulation foam. Also, 1,1,2-trichloro-1,2,2-trifluoroethane (known in art as CFC-113) is currently available in commercial quantities and is used as a solvent for cleaning integrated circuit boards. Currently, 1,1-dichloro-1-fluoroethane (known in the art as HCFC-141b) is considered to be a replacement for CFC-11 and CFC-113 because HCFC-141b does not deplete ozone in the stratosphere to the same extent as CFC-11 or CFC-113. Because the demand for HCFC-141b will increase dramatically in the future, commercially viable processes for the preparation of pure HCFC-141b are needed.

HCFC-141b may be produced by reacting vinylidene chloride with anhydrous hydrogen fluoride. The reaction is expressed by the following equation:

HCFC-141b may also be produced by reacting 1,1,1-trichlorothane with anhydrous hydrogen fluoride. The reaction is expressed by the following equation:

When vinylidene chloride is used, dichloroacetylene is present as an impurity in the feed stock and survives the reaction for the preparation of 1,1-dichloro-1-fluoroethane. Dichloroacetylene also passes normal purification processes such as distillation and ends up in the final product.

Regardless of whether 1,1-dichloro-1-fluoroethane is prepared by using vinylidene chloride or 1,1,1-trichloroethane with anhydrous hydrogen fluoride. vinylidene chloride is always present as an impurity in the final product. When vinylidene chloride is used as a starting material, residual amounts of unreacted vinylidene chloride are present in the final product. When 1,1,1-trichloroethane is used as a starting material, thermal decomposition of 1,1,1-trichloroethane results in the formation of small amounts of vinylidene chloride which are present in the final product. Because vinylidene chloride has a boiling point of 31.5° C. and 1,1-dichloro-1-fluoroethane has a boiling point of 32° C., removal of vinylidene chloride from 1,1-dichloro-1-fluoroethane is very difficult.

Dichloroacetylene is a very unstable and extremely toxic compound. Dichloroacetylene is mutagenic and has high carcinogenic potential. The Threshold Limit Value (TLV) for exposure to DCA is 0.1 part per million. Dichloroacetylene present in 1,1-dichloro-1-fluoroethane after distillation varies from 5 to 20 parts per million.

Vinylidene chloride is also a very toxic compound. Excessive exposure may cause damage to the kidneys, liver, or central nervous system. The TLV for exposure to vinylidene chloride is 5 parts per million. Vinylidene chloride present in 1,1-dichloro-1-fluoroethane after distillation varies from 500 to 1,200 parts per million. Although full scale toxicity studies for 1,1-dichloro-1-fluoroethane are currently incomplete, the Panel for Advancement of Fluorocarbon Test (PAFT II). which defines the purity of the 1,1-dichloro-1-fluoroethane product, has set current specifications on dichloroacetylene and vinylidene chloride at 1 part per million and 200 parts per million, respectively.

As such, a need exists for a process for removing or reducing the amounts of dichloroacetylene and vinylidene chloride in the 1,1-dichloro-1-fluoroethane product.

The purification of halogenated hydrocarbons has been the subject of many references. In general, these processes relate to the removal of reaction by-products which are difficult to remove by ordinary methods.

U.S. Pat. No. 2,879,228 teaches that hydrogen-containing impurities are removed by contact with alumina or silica gel at a temperature of 100° to 250° C. The impurities are adsorbed by the alumina or silica so as to leave a purified perfluorinated hydrocarbon.

Japanese Patent Application No. 48-103,502 teaches that sodium carbonate solutions are used to treat perchlorofluoroalkanes such as trichlorotrifluoroethane at 25° to 60° C. to remove hydrogen-containing halogenated hydrocarbons.

U.S. Pat. No. 3,696,156 teaches that alumina with 0.1 to 5% of an alkali metal or alkaline earth metal is used to remove unsaturated impurities to below 2 parts per million.

West German DE No. 3,017,531 teaches the purification of contaminated refrigerants such as trichlorotrifluoroethane by contact with alumina and an alkaline earth.

West German DE No. 3,311,751 teaches that a zeolite having a pore size of 0.4 to 1 nm is useful for removing halogens and inorganic halides from fluorochlorocarbons such as trichlorotrifluoroethane.

Japanese Patent No. 83-035,737 teaches regeneration of a zeolite used to purify and dry trichloroethane.

Russian Patent SU No. 743,985 teaches that chlorinated and fluorinated organic solvents are purified by passing the solvents in the vapor phase over activated charcoal in the presence of phosphorus pentoxide.

Commonly assigned U.S. Pat. No. 4,849,558 teaches that chlorofluorocarbon solvents such as 1,1,2-trichloro-1,2,2-trifluoroethane may be purified by removing sulfur dioxide by contact with alumina or zeolites.

Faced with the present problem, we considered various purification processes including selective adsorption. Selective adsorption requires an adequate balance between the polarity and pore size of the adsorbent and the dipole moments and molecular sizes of the adsorbates and solvent. The polarity and pore size of the adsorbent have to match the dipole moments and molecular sizes of dichloroacetylene and vinylidene chloride and to mismatch the dipole moment and molecular size of 1,1-dichloro-1-fluoroethane in order to absorb dichloroacetylene and vinylidene chloride selectively from 1,1-dichloro-1-fluoroethane. The dipole moment of dichloroacetylene is estimated to be 0.07 debye and the molecular size is 60 angstroms$^3$. The dipole moment of vinylidene chloride is 1.34 debye and the molecular size is calculated to be 70 angstroms$^3$. The dipole moment 1,1-dichloro-1-fluoroethane is 2.14 debye and the molecular size is 82 angstroms$^3$.

We believed that molecular sieves which are made from a mixture of aluminum oxide and silicon dioxide and have a nominal pore size ranging from 3 to 5 angstroms would match the dipole moments and molecular sizes of dichloroacetylene and vinylidene chloride and mismatch 1,1-dichloro-1-fluoroethane so as to selectively absorb dichloroacetylene and vinylidene chloride from the 1,1-dichloro-1-fluoroethane. As set forth below in the Comparatives, molecular sieves were incapable of selectively absorbing dichloroacetylene and vinylidene chloride.

We then believed that silicalite which is made mainly from silica and has a pore size of about 5 to 6 angstroms would match the dipole moments and molecular sizes of dichloroacetylene and vinylidene chloride and mismatch 1,1-dichloro-1-fluoroethane so as to selectively absorb dichloroaetylene and vinylidene chloride from the 1,1-dichloro-1-fluoroethane. As set forth below in the Comparatives, silicalite was incapable of selectively absorbing dichloroacetylene and vinylidene chloride.

SUMMARY OF THE INVENTION

It was then surprising when we found that activated carbon was capable of selectively absorbing dichloroacetylene and vinylidene chloride from 1,1-dichloro-1-fluoroethane. As such, the present invention provides a process for the purification of 1,1-dichloro-1-fluoroethane comprising the steps of:

(a) reacting anhydrous hydrogen fluoride with 1,1,1-trichloroethane or vinylidene chloride containing dichloroacetylene to form 1,1-dichloro-1-fluoroethane; and (b) passing 1,1-dichloro-1-fluoroethane through activated carbon to substantially remove unsaturated impurities. The present invention provides a process for reducing the amounts of dichloroacetylene and vinylidene chloride in the 1,1-dichloro-1-fluoroethane product so as to meet the current specifications set forth by the panel for Advancement of Fluorocarbon Test.

It is accordingly an object of this invention to provide a process for the substantial removal of unsaturated compounds from 1,1-dichloro-1-fluoroethane.

A further object of the present invention is to provide a process for the substantial removal of dichloroacetylene and vinylidene chloride from 1,1-dichloro-1-fluoroethane.

Other objects and advantages of the invention will become apparent from the following description.

DETAILED DESCRIPTION OF THE INVENTION

The first step of the present process involves reacting anhydrous hydrogen fluoride with 1,1,1-trichloroethane or vinylidene chloride to form 1,1-dichloro-1-fluoroethane. When 1,1,1-trichloroethane is used as the starting material, 17 grams hydrogen fluoride and 3.73 grams 1,1,1-trichloroethane are reacted at 110° C. for 15 minutes to form 1,1-dichloro-1-fluoroethane; see U.S. Pat. No. 3,833,676 which is incorporated herein by reference to the extent necessary to complete this disclosure. When vinylidene chloride is used as a starting material, four moles of hydrogen fluoride are reacted with vinylidene chloride for three hours at 65° C. to form 1,1-dichloro-1-fluoroethane; see A. L. Henne et al., *J. Am. Chem. Soc.* 65, 1272 (1943). Commercially available anhydrous hydrogen fluoride; 1,1,1-trichloroethane; and vinylidene chloride may be used in the preparation. As discussed earlier. dichloroacetylene is present as an impurity in vinylidene chloride and survives the 1,1-dichloro-1-fluoroethane preparation process.

Preferably after preparation of 1,1-dichloro-1-fluoroethane, the resulting 1,1-dichloro-1-fluoroethane is distilled in order to remove impurities such as hydrogen fluoride and high boilers including tars.

The second step of the present process involves passing the 1,1-dichloro-1-fluoroethane through activated carbon to essentially remove unsaturated impurities. Preferably, the removed unsaturated impurities are vinylidene chloride and dichloroacetylene. Commercially available activated carbon is useful in the present process. The adsorption efficiency and adsorption capacity of the activated carbon depend upon the particle size of the activated carbon in a dynamic flow system. Preferably, the activated carbon has a particle size range of about 0.005 millimeter to about 10 millimeters. More preferably, the activated carbon has a particle size range of about 0.04 millimeter to about 5 millimeters. Most preferably, the activated carbon has a particle size range of about 0.1 millimeter to about 2 millimeters. The adsorption capacity of a given activated carbon may also be improved by removing the ash content of the carbon this may be done by a standard technique such as acid wash.

An activated carbon having a particle size range of 0.595 millimeters × 1.68 millimeters (12×30 mesh) is available from the Calgon Corporation as Calgon PCB (Pittsburgh coconut based) carbon. Another activated carbon having a particle size range of 0.105 millimeters × 0.595 millimeters (30×140 mesh) is available from the Calgon Corporation as Calgon PCB (Pittsburgh coconut based) carbon. Another activated carbon having a particle size range of 0.42 millimeters × 1.68 millimeters (12×40 mesh) is available from the Calgon Corporation as Calgon CAL (bituminous coal based) carbon.

Regardless of whether 1,1,1-trichloroethane or vinylidene chloride is used in the preparation of 1,1-dichloro-1-fluoroethane, after distillation the 1,1-dichloro-1-fluoroethane contains from about 500 to about 1,200 parts per million of vinylidene chloride. The 1,1-dichloro-1-fluoroethane prepared from vinylidene chloride contains from about 5 to about 20 parts per million of dichloroacetylene. By practicing the present process, the amounts of dichloroacetylene in 1,1-dichloro-1-fluoroethane are drastically reduced if not completely removed and the amounts of vinylidene chloride in 1,1-dichloro-1-fluoroethane are reduced to a of less than about 200 parts per million.

After performing the second step of the present process, the resulting 1,1-dichloro-1-fluoroethane may be further distilled.

The purification is typically run at room temperature and atmospheric pressure and thus, the 1,1-dichloro-1-fluoroethane is in the liquid phase. Unlike known purification processes where the activated carbon is preheated to a temperature of 300° C. to 400° C., heating is unnecessary in the present purification step. Because the activated carbon does heat up during the purification step, the activated carbon is typically chilled in order to keep it at room temperature. Also unlike known processes where the purification is run in the presence of phosphorus pentoxide, the presence of phosphorus pentoxide is unnecessary in the present purification step.

The purification may be conducted in batch or continuous fashion.

The purified 1,1-dichloro-1-fluoroethane produced by the present process is useful as a blowing agent for the production of rigid urethane thermoinsulation foam. See for example U.S. Pat. Nos. 4,271,273; 4,652,589; 4,686,240; 4,699,932; 4,701,474; 4,717,518; and 4,727,094. The purified 1,1-dichloro-1-fluoroethane is also useful for cleaning solid surfaces by treating the surfaces in any manner known in the art such as by dipping or spraying.

The present invention is more fully illustrated by the following non-limiting Examples.

COMPARATIVES A-E AND EXAMPLE 1

For Comparative A, a molecular sieve supplied by Union Carbide, made from a mixture of aluminum oxide and silicon dioxide, and having a nominal pore size of 3 angstroms was used. For Comparative B, a molecular sieve supplied by Union Carbide, made from a mixture of aluminum oxide and silicon dioxide, and having a nominal pore size of 4 angstroms was used. For Comparative C, a molecular sieve supplied by Union Carbide, made from a mixture of aluminum oxide and silicon dioxide, and having a nominal pore size of 5 angstroms was used. For Comparative D, a silicalite type SP-115 supplied by Union Carbide and made from aluminum-bound silica was used. For Comparative E, a silicalite type SR-115 supplied by Union Carbide and made from silica-bound silica was used.

For Example 1, activated carbon supplied by Calgon Corporation, designated as PCB (pittsburgh coconut based), and having a particle size range of 0.595 millimeters × 1.68 millimeters (12×30 mesh) was used.

The adsorbent was dried in a vacuum oven at a temperature between 110° and 150° C. for 24 to 72 hours. After drying, the adsorbent was packed in a glass column having a length of 48 centimeters and a diameter of 3.9 centimeters. A 250 milliliter adding funnel and a 46 centimeter long condenser were equipped on the top of the absorption column. An impure 1,1-dichloro-1-fluoroethane prepared from vinylidene chloride and hydrogen fluoride was used. The impure 1,1-dichloro-1-fluoroethane contained 875 parts per million vinylidene chloride and 13 parts per million dichloroacetylene. About 250 to 500 milliliters of the impure 1,1-dichloro-1-fluoroethane were passed through the absorption column.

For the Comparatives, the first 50 to 100 milliliters of 1,1-dichloro-1-fluoroethane eluted through the adsorption column were collected and analyzed for the concentration of vinylidene chloride and/or dichloroacetylene; the results are in Table I below. The last 50 milliliters were also collected and analyzed; as expected, the amounts of vinylidene chloride were higher in the last 50 milliliters than in the first 50 milliliters. For Example 1, the first and the last 50 to 100 milliliters of the eluted samples were collected and analyzed; the results are in Table I below.

Vinylidene chloride is abbreviated as VdCl$_2$ and expressed in parts per million (ppm) and dichloroacetylene is abbreviated as DCA and expressed in parts per million (ppm) in Table I.

The collected 1,1-dichloro-1-fluoroethane was first analyzed for vinylidene chloride and if the level was below 200 parts per million, the sample was then analyzed for dichloroacetylene. If the level was above 200 parts per million, the sample was not analyzed for dichloroacetylene (abbreviated as NA in Table 1). ND stands for not detectable.

TABLE I

| COMP./EX. | ABSORBENT | VdCl2(ppm) | DCA(ppm) |
|---|---|---|---|
| HCFC-141b | — | 875 | 13 |
| A | molecular sieve 3A | 651 | NA |
| B | molecular sieve 4A | 1021 | NA |
| C | molecular sieve 5A | 585 | NA |
| D | silicalite SP-115 | 410 | NA |
| E | silicalite SR-115 | 380 | NA |
| 1 | activated carbon | ND | ND |

The molecular sieve of Comparative B adsorbed more 1,1-dichloro-1-fluoroethane than vinylidene chloride which resulted in a higher vinylidene chloride concentration in the eluted sample compared with the original sample. For Example 1, no vinylidene chloride or dichloroacetylene was detected in either the first or the last 50 milliliters of the eluted sample.

EXAMPLE 2

Example 1 was repeated except that the adding funnel was replaced by another 46 centimeter long condenser. A small pump was used to pump the impure 1,1-dichloro-1-fluoroethane to the apparatus continuously. 229 grams of the activated carbon used in Example 1 were packed into the glass column. An impure 1,1-dichloro-1-fluoroethane sample was prepared so as to contain 3080 parts per million vinylidene chloride which is higher than the normal concentration. As the impure 1,1-dichloro-1-fluoroethane sample was continuously pumped and eluted through the packed carbon bed at about 29 grams/minute, instantaneous samples were taken and analyzed to determine the amount of vinylidene chloride. No analysis of dichloroacetylene was done for this experiment. The results are in Table II below.

TABLE II

| ELUTION WEIGHT OF IMPURE HCFC-141b (grams) | VdCl2 (ppm) |
|---|---|
| 250 | 300 |
| 480 | 600 |
| 720 | 1,100 |
| 960 | 1,500 |

EXAMPLE 3

Example 2 was repeated except that activated carbon supplied by Calgon Corporation, designated as PCB (Pittsburgh coconut based). and having a particle size range of 0.105 millimeters × 0.595 millimeters (30×140 mesh) was used. 222 grams of the activated carbon were packed into the column. An impure 1,1-dichloro-1-fluoroethane containing 875 parts per million of vinylidene chloride and 13 parts per million of dichloroacetylene, which are normal amounts, were pumped continuously through the carbon bed at about 18.2 grams/minute. Instantaneous samples eluted through the column were collected for analysis. The results are in Table III below.

Vinylidene chloride is abbreviated as VdCl$_2$ and expressed in parts per million (ppm) and dichloroacetylene is abbreviated as DCA and expressed in parts per million (ppm) in Table III. ND stands for not detectable.

TABLE III

| ELUTION WEIGHT OF IMPURE HCFC-141b (grams) | VdCl2 (ppm) | DCA (ppm) |
|---|---|---|
| original HCFC-141b | 875 | 13 |
| 23 | 40 | ND |
| 193 | 34 | ND |
| 427 | 29 | ND |
| 624 | 28 | ND |
| 801 | 12 | ND |

No dichloroacetylene was detected in any of the purified samples. Also, the concentration of vinylidene chloride in each sample was well below the 200 parts per million level.

EXAMPLE 4

Example 3 was repeated except that activated carbon supplied by Calgon Corporation, designated as CAL (bituminous coal based activated carbon), and having a particle size range of 0.42 millimeters × 1.68 millimeters (12 × 40 mesh) was used. 230 grams of the activated carbon were packed into the column. The same impure 1,1-dichloro-1-fluoroethane as used in Example 3 was pumped continuously through the packed carbon bed. Instantaneous samples eluted through the column were collected and analyzed for dichloroacetylene and vinylidene chloride. The results are in Table IV below.

TABLE IV

| ELUTION WEIGHT OF IMPURE HCFC-141b (grams) | VdCl2 (ppm) | DCA(ppm) |
|---|---|---|
| original HCFC-141b | 875 | 13 |
| 105 | 7 | ND |
| 342 | 47 | ND |
| 728 | 120 | ND |
| 994 | 154 | ND |

Although this activated carbon is effective in removing dichloroacetylene, it is not as effective in removing vinylidene chloride.

Having described the invention in detail by reference to preferred embodiments thereof, it will be apparent that modifications and variations are possible without departing from the scope of the invention defined in the appended claims.

What is claimed is:

1. A process for the purification of 1,1-dichloro-1-fluoroethane comprising the steps of:
   (a) reacting anhydrous hydrogen fluoride with 1,1,1-trichloroethane or vinylidene chloride containing dichloroacetylene to form said 1,1-dichloro-1-fluoroethane; and
   (b) passing said 1,1-dichloro-1-fluoroethane through activated carbon to substantially remove unsaturated impurities.

2. The process of claim 1 wherein before said step (b), said 1,1-dichloro-1-fluoroethane is distilled.

3. The process of claim 1 wherein after said step (b), said 1,1-dichloro-1-fluoroethane is distilled.

4. The process of claim 1 wherein said unsaturated impurities are dichloroacetylene and vinylidene chloride.

5. The process of claim 1 wherein said unsaturated impurities are dichloroacetylene.

6. The process of claim 1 wherein said unsaturated impurities are vinylidene chloride.

7. The process of claim 1 wherein said activated carbon has a particle size range of about 0.005 millimeter to about 10 millimeters.

8. The process of claim 1 wherein said activated carbon has a particle size range of about 0.04 millimeter to about 5 millimeters.

9. The process of claim 1 wherein said activated carbon has a particle size range of about 0.1 millimeter to about 2 millimeters.

10. The process of claim 2 wherein after said step (b), said dichloroacetylene is completely removed from said 1,1-dichloro-1-fluoroethane.

11. The process of claim 2 wherein after said step (b), the concentration of said vinylidene chloride in said 1,1-dichloro-1-fluoroethane is less than about 200 parts per million.

12. The process of claim 1 wherein said activated carbon has a particle size range of about 0.595 millimeter to about 1.68 millimeters.

13. The process of claim 1 wherein said activated carbon has a particle size range of about 0.105 millimeter to about 0.595 millimeter.

14. The process of claim 1 wherein said activated carbon has a particle size range of about 0.42 millimeter to about 1.68 millimeters.

* * * * *